United States Patent [19]

Dunstan et al.

[11] 4,361,984

[45] Dec. 7, 1982

[54] MICROPROPAGATION OF PLANT MATERIAL

[75] Inventors: David I. Dunstan, Winfield; Keith E. Turner, Kelowna; David W. Lane, Summerland, all of Canada

[73] Assignee: Kelowna Nurseries Ltd., Kelowna, Canada

[21] Appl. No.: 290,544

[22] Filed: Aug. 6, 1981

[51] Int. Cl.³ .............................................. A01G 1/00
[52] U.S. Cl. ........................................................ 47/58
[58] Field of Search ............................................ 47/58

[56] References Cited

U.S. PATENT DOCUMENTS 4,152,869  5/1979  Jones ....................................... 47/58

*Primary Examiner*—Robert E. Bagwill
*Attorney, Agent, or Firm*—Townsend and Townsend

[57] ABSTRACT

A process for the micropropagation of plant material. The process comprises excising a shoot tip having a length in the range 0.6 to 3 millimeters from a bud of the plant. The excised tip is placed in a first nutrient medium containing benzyl adenine to induce shoot elongation and the elongated shoot decapitated. The decapitated shoot is placed in a nutrient medium to stimulate lateral shoot induction and elongation. Shoots one centimeter or more are excised and the excised shoots are implanted in a rooting nutrient medium for root production.

14 Claims, No Drawings

MICROPROPAGATION OF PLANT MATERIAL

FIELD OF THE INVENTION

This invention relates to a process for propagating plant material, in particular a process for the commercial micropropagation of rosaceous fruit cultivars with application to forest trees. The procedure has been developed for commercial use with tree fruit cultivars, both root stock and scion stock, though it is applicable to other fruit species and to other woody plant materials, including coniferous and angiosperm tree species.

DESCRIPTION OF THE PRIOR ART

Jones, in U.S. Pat. No. 4,152,869 issued May 8th, 1979, describes a process for propagating woody plant material that includes setting a shoot on a nutrient medium including cytokinin, an auxin and a phenolic compound to produce a number of shoots. The shoots are excised and allowed to multiply any desired number of times. Individual shoots are then excised and rooted on the same or a similar nutrient medium but from which the cytokinin is omitted. The resulting plants are finally grown on. Jones's invention is described as being particularly valuable in connection with newly bred varieties. When a new variety of root stock is bred the number of available plants will generally be extremely limited and it may well take 5 to 10 years to produce a sufficient supply to satisfy the market by methods existing prior to Jones. In the preferred form of the Jones process, the invention enables about 15 shoots to be grown in eight weeks from a single shoot and shoots may then be multiplied about five fold monthly. Jones thus claims that it may be possible to obtain more than 100 thousand shoots from a single tip within 12 months.

SUMMARY OF THE INVENTION

The present invention seeks to provide improvements in the Jones process and, in particular, provides an even greater rate of growth. The procedure according to the invention is particularly of use where the clonal propagation of plants is required either to ensure a true to original production of propagules to satisfy early introduction on the market for existing market demands or where a consistent crop yield and uniform response is required.

Accordingly, in a first aspect, the present invention is a process for micropropagation of plant material comprising: excising a shoot tip having a length in the range 0.6 to 3 millimeters from a bud of the plant; placing the excised tip in a first nutrient medium containing benzyl adenine to induce shoot elongation; decapitating the elongated shoot; placing the decapitated shoot in a nutrient medium to stimulate lateral shoot induction and elongation; excising shoots one centimeter or more; and implanting the excised shoots in a rooting nutrient medium for root production.

It is of particular significance that the process of the present invention may, in a preferred aspect, be used with dormant buds. Jones, for example, applies his process to shoots or to flushed buds but these can give problems in sterilization and, in particular, require cautious sterilization. This is not so in the process of the present application as the dormant buds used according to a preferred aspect are protected by bud scales.

DESCRIPTION OF THE PREFERRED EMBODIMENTS

A specific embodiment of the invention will be described, merely by way of example:

A nutrient formulation, after Murashige and Skoog, was prepared having the following composition:

|  |  | mg. per liter |
|---|---|---|
| Ammonium nitrate | $NH_4NO_3$ | 1650.0 |
| Potassium nitrate | $KNO_3$ | 1900.0 |
| Magnesium sulphate | $MgSO_4 7H_2O$ | 370.0 |
| Manganese sulphate | $MnSO_4 4H_2O$ | 22.3 |
| Zinc sulphate | $ZnSO_4 7H_2O$ | 8.6 |
| Copper sulphate | $CuSO_4 5H_2O$ | 0.025 |
| Calcium chloride | $CaCl_2 2H_2O$ | 440.0 |
| Potassium iodide | $KI$ | 0.83 |
| Cobalt chloride | $CoCl_2 6H_2O$ | 0.025 |
| Potassium dihydrogen orthophosphate | $KH_2PO_4$ | 170.0 |
| Boric acid | $H_3BO_3$ | 6.2 |
| Sodium molybdate | $Na_2MoO_4 2H_2O$ | 0.25 |
| Iron sulphate | $FeSO_4 7H_2O$ | 27.84 |
| Sodium ethylenediaminetetra-acetic acid | $Na_2EDTA$ | 37.24 |
| Sucrose |  | 30000. |
| Glycine |  | 2.0 *a |
| Indole-acetic acid (salt-free) |  | 1–30 *b |
| Kinetin |  | 0.04–10 *c |
| Agar |  | 10000. *d |
| myo-inositol |  | 100. |
| Nicotinic acid |  | 0.5 |
| Pyridoxine HCl |  | 0.5 *e |
| Thiamine HCl |  | 0.1 |

*a usually removed
*b sometimes removed
*c removed
*d 8,000
*e 0.1

In addition to the above, according to species and required responses, the following may be added:

6 benzyl adenine (salt-free) 6BA: 0–5.0
αnaphthalene acetic acid (salt-free) NAA: 0–5.0
indole-butyric acid (salt-free) IBA: 0–5.0

The pH of this medium was adjusted to 5.5 to 6.5, depending on species, and autoclaved for 15 minutes at 121° C. and 15 pounds per square inch pressure. It should be noted that no components of the medium need be separately filter-sterilized.

The following plant material has been used for evaluation of various stages in the process, all the material listed was field grown:

| EXPERIMENTAL PROCEDURE | |
|---|---|
| apple rootstock: | M26, M9, M7, M111, M4, M2 Antonovka (all virus-certified) |
| apple scionstock: | McIntosh Spur type McIntosh and Spur type red delicious apple. (virus-certified) |
| apple ornamental: | Dolgo (virus-certified) |
| cherry rootstock: | Mahaleb, Mazzard F12/1. (virus-certified) |
| cherry scion: | Bing, Montmorency Hobbs, (virus certified) |
| pear scion: | Bartlett, D'Anjou (virus certified) |
| plum rootstock: | Myrobolan B (virus certified) |
| peach scion: | Redhaven, Fairhaven (virus certified) |
| grape scion: | Muller Thurgau, Veeblanc, Cayuga White |
| ornamentals: | *Spiraea bulmada, Magnolia soulangiana* |
| Forest species: | Radiata pine, Spruce, Douglas Fir, |

| EXPERIMENTAL PROCEDURE |
|---|
| -continued |
| Lodgepole pine. |

METHOD

Dormant buds from tree-fruit cultivars can be adequately sterilized using commercial sodium hypochlorite solutions which are diluted to provide chlorine concentrations ranging from 0.42% (used with the smaller more tender buds) to 1.5% (used with larger, more waxy, and tightly closed buds). Prior to sterilization, outer bark surfaces adjacent to the bud, and the outermost bud scales, are removed, and a bud chip is subsequently excised. Immersion in sterilant can be from 8 minutes (generally for use with more concentrated solutions, or more tender buds) to 20 minutes (generally for use with milder solutions). Sterilant action is terminated by immersion in a series of three sterilized distilled water washes.

There is no requirement for a double sterilization procedure.

Following the washes the inner scales and outer primordia for dormant bud material are removed aseptically with the aid of a binocular microscope, until a 1–2 mm explant can be excised which comprises the apical meristem dome with one to several inner primordia.

The base of each tip is pushed into nutrient medium containing benzyl adenine, alone or in combination with indole acetic acid. Cultures are placed under the growth room conditions of 16 hours light: 8 hours dark (550 lumen) at 25° C.±2° C. After three weeks the majority of buds have grown to 0.75–1.0 cm. in height at which time they are removed (subcultured) from the exhausted nutrient medium and placed into fresh nutrient medium with the same growth regulators. After a subsequent 21–28 days shoots have elongated sufficiently to permit dissection at subculture which produces apical tips, and a 2–5 node stem fragment. The stem fragment is placed in an inverted position, the apex is placed vertically. This promotes a release of apical dominance, simulating a basipetal growth regulator flow.

Following 21 days plant material proliferates sufficiently to permit excision of 5–10 new apical tips, their basal stem fragments, and the associated main branch system which has supported them. All three explant types are recycled, marking the initiation of the continually replenishing system which routinely produces up to 10 new apical tips and their stem fragments each subsequent 21 days. At this time it is possible to culture with the addition of benzyl-adenine alone, usually by regularly adjusting the benzyladenine level each 21 days to obtain best growth.

The various explant types form part of a replenishing cycle. Tip and stem fragments give rise to young stem ("stump") masses. These provide further tips, and stem fragments and themselves give rise to older "stumps". The latter category are either used to replenish the cycle in the build-up stages of commercialization, or they are the source of shoots for rooting in the production stage.

Shoots from 1–2.5 cm in height can subsequently be excised for inoculation into ¼ to ¾ the strength of the nutrient formulation noted, containing base-free auxin-like plant growth regulators. The concentrations and type of auxin vary considerably from species to species and from variety to variety. The process of the invention also employs alternatives to this rooting procedure by dipping the freshly cut ends of shoots in dilute auxin overnight and soaking freshly cut shoots in concentrated auxin for a few hours. In each case the unrooted shoots are planted immediately after treatment.

Rooting becomes apparent between 10 and 21 days following the inoculation at which time shoots are removed for planting in a nutrient containing mixture of peat, perlite and sand (3:4:1 by volume) in 5×5 cm plastic pots in trays of 36 pots each. Trays are placed beneath an intermittent mist regime in a growth room. An initially high misting frequency (once per minute) is reduced over 7 days to once each 20 to 30 minutes at which time the trays are removed from the mist and are grown on under growth room conditions.

Plant growth is good following removal from the mist bench, achieving a height of 10–15 cm. in 28–35 days.

The above process details required levels for several fruit tree species. Using the process it is possible to establish the plant material in culture, to obtain a flourishing culture that can produce up to 10 shoots per original during a 21 to 28 day culture period as part of a continuously replenishing cycle capable of producing in excess of one million plants during a year from inception and, of course, more than that in subsequent years.

The advantages of the present invention, for example as compared with the prior art as exemplified by Jones in U.S. Pat. No. 4,152,869 referred to above, are numerous. For example the process of the present invention can use dormant buds. Flushed buds, as used in Jones, for example are more delicate and require a more cautious sterilization than dormant buds which are protected by bud scales. Flush buds are usually only the terminal buds whereas dormant buds can be any bud material, lateral or terminal. It follows that a greater volume of material can be used in the process of the present invention.

The reliability of sterilization with the method of the present invention and reduction of complexity in sterilization as compared with the Jones method, is practically of great importance. Using dormant bud material the buds can be sterilized to provide 80% to 100% survival. Flushed buds however have consistently caused sterilization problems which accounts for the dual sterilization described in the Jones patent. Hitherto it was thought to be impossible to grow dormant buds in cultures simply because they were dormant. However, the process of the present invention removes the dormancy factor—presumed to be in the bud scales—and provides a cytokinin, which duplicates springtime flushing conditions. Perhaps most important, whereas dormant buds can be found throughout the year—dormancy referring to the resting state of the buds—flush buds are usually restricted to the growing season although it must be admitted that they can be obtained by confining mother material in warmed greenhouses to induce flushing.

The above U.S. patent requires a six week period in a rooting medium. From a commercial point of view this uses a great deal of space and bottles. In comparison with a monthly growth of the cycle in the Jones patent the rooting phase clearly provides a limiting factor. Furthermore, a six week cycle permits only one or two spring-time plantings. However, in the process of the invention it is possible to remove some rooted plant material, for example grapes, within ten days and others in up to 21 days, for example apples and cherries. This prevents a bottleneck in the process when compared with the 28 day growth cycle of Jones. Thus, spring plantings could extend to three or four. In addition, the shorter time in rooting medium and the rapid passage through misting and growing on stages in the process of the present invention allows the invention to produce a greater number of units for a given capital expenditure, putting through approximately 12½ cycles per year compared to 8½ of Jones. The process also permits flexibility in terms of altering quantities and cultivar type should it be necessary.

The quality of roots and the rapidity of growth after six weeks on rooting medium is believed to be poor in the Jones process. Root initiation has proceeded so well in the 10 to 21 days necessary in the process of the present invention that this is considered optimum for transplanting. Longer roots, associated with longer time in culture as in Jones, produce difficulties in removing agar medium and in planting them. The shorter the roots the better. Further, when plants in the process of the present invention are removed from their dilute rooting medium they have already been partially prepared for rapid growth subsequent to transplantation. This is not believed to be the case in the Jones process.

The inversion technique used in the process of the present invention is invaluable in the early stages and bulking up stages of culture. No adequate theoretical background can be provided as theories for the hormonal control of plant growth are varied. Usually it is thought that different growth responses occur when different threshold ratios of cytokinin: auxin concentration are required in different plant organs. Apical dominance is believed to be due to a basipetal auxin flow which dilutes itself with distance along the stem. Thus, generally only shoots quite a way down a branch will break bud. However, dormancy can be broken by external application of cytokinin. In either case it is probably the predominance of the one hormone over the other that produces the effect. While it is known that shoot translocation of auxins is generally basipetal, it is not fully understood how cytokinin is translocated. In the process of the invention the cytokinin: auxin ratio still affects the growth response but whereas the present process uses cytokinin (generally synthesized by roots in addition to apices) it is believed that the plant manufactures its own auxin in its apices. By decapitating the young shoots that develop from sterilized buds and during the bulk-up stages the process of the present invention simulates pruning conditions, releasing the decapitated portions from apical dominance and thus lowering the auxin. This decapitation also imbalances the cytokinin: auxin ratio by adding cytokinin and by inverting the decapitated shoot portions a basipetal message for growth and bud break is simulated. If shoots were left entire they would have to elongate considerably before any lateral bud break was achieved unless they had a low cytokinin threshold. This would require longer time in culture. The inventors have also found difficult-to-culture shoots and shoots that require invigoration respond more favourably to inversion than to other techniques.

The Jones references teaches the use of phenolic compounds. However, the process of the present invention does not require such compounds. Generally their use is undesirable because they require a lengthy and risky process of filter sterilization. Gibberellic acid is also taught by Jones and also requires filter sterilization. Although it is attributed with the role of stem elongation and dormancy breaking applicants have found that cytokinin alone, at least for the process of the present invention, is sufficient.

Further the invention allows plants that have obtained a height of 10 to 15 centimeters to be field planted during the growing season within one to two months from removal from the culture vessel. The field grown plants can be grafted within one growing season or can be used to provide planting of self-rooted scion varieties. A particularly important advantage of the present invention is that it allows a year round production of plants. This is in marked contrast to traditional production, which is limited to a shorter growing season. One effect of this is it allows a low inventory of plant materials to be held for rapid multiplication to meet fluctuating market demands.

The process also permits the early introduction of recently developed plant material. Plants may be grown on after the implanting of the excised shoots in rooting nutrient medium for root production or the product of that implanting may simply be stored in a refrigerator until required, for example as dictated by market requirements.

We claim:
1. A process for the microfpropagation of plant material comprising:
   excising a shoot tip having a length in the range 0.6 to 3 millimeters from a bud of the plant;
   placing the excised tip in a first nutrient medium containing benzyl adenine to induce shoot elongation;
   decapitating the elongated shoot;
   placing the decapitated shoot in a nutrient medium to stimulate lateral shoot induction and elongation;
   excising shoots one centimeter or more; and
   implanting the excised shoots in a rooting nutrient medium for root production.
2. A process as claimed in claim 1 in which the bud is selected from all vegetative material including dormant flushing and flush buds, lateral or terminal buds from lateral or terminal shoots, vegetative or floral buds.
3. A process as claimed in claim 1 in which the bud is a dormant bud.
4. A process as claimed in claim 3 in which the outer bark surfaces adjacent the dormant bud and the outermost bud scales are removed and a bud chip subsequently excised.
5. A process as claimed in claim 1 in which the shoot tip has a length in the range 1 to 2 millimeters.
6. A process as claimed in claim 1 in which the shoot tip includes a meristem, at least one leaf primordia subtended by a woody cube.
7. A process as claimed in claim 1 in which the excision of the shoot tip is carried out under a microscope.
8. A process as claimed in claim 1 in which the rooting nutrient medium contains a base free auxin but no other added known plant growth substance.
9. A process as claimed in claim 8 in which the auxin is selected from indole acetic acid, naphthelene acetic acid and indole butyric acid.
10. A process as claimed in claim 1 in which the decapitated shoot is placed in the nutrient medium in an inverted position.
11. A process as claimed in claim 1 including a single preliminary sterilization step on the bud.
12. A process as claimed in claim 1 including growing on the plants.
13. A process as claimed in claim 1 including refrigerating the product so that it may be stored for future growing on.
14. A process as claimed in claim 1 in which the rooting nutrient medium is the first nutrient medium diluted.

* * * * *